United States Patent
Agyare et al.

(10) Patent No.: US 12,227,492 B1
(45) Date of Patent: Feb. 18, 2025

(54) PYRIMIDINE NUCLEOSIDES AS ANTICANCER AGENTS AGAINST PANCREATIC CANCER

(71) Applicant: Florida A&M University, Tallahassee, FL (US)

(72) Inventors: Edward Agyare, Tallahassee, FL (US); Xue You Zhu, Tallahassee, FL (US); Andriana Inkoom, Tallahassee, FL (US); Nkafu Bechem Ndemazie, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 293 days.

(21) Appl. No.: 17/744,882

(22) Filed: May 16, 2022

Related U.S. Application Data

(60) Provisional application No. 63/188,563, filed on May 14, 2021.

(51) Int. Cl.
  *C07D 405/04* (2006.01)
  *A61K 31/513* (2006.01)
  *A61P 35/00* (2006.01)

(52) U.S. Cl.
  CPC .......... *C07D 405/04* (2013.01); *A61K 31/513* (2013.01); *A61P 35/00* (2018.01)

(58) Field of Classification Search
  CPC ...... C07D 405/04; A61K 31/513; A61P 35/00
  See application file for complete search history.

(56) References Cited

PUBLICATIONS

Yu et al. Comprehensive transcriptomic analysis of cell lines as models of primary tumors across 22 tumor types. Nature Communications. vol. 10: No. 3574, pp. 1-11. (Year: 2019).*
Shichi, Yuuki et al. Epithelial and Mesenchymal Features of Pancreatic Ductal Adenocarcinoma Cell Lines in Two-and Three-Dimensional Cultures. J. Pers. Med. 2022, 12, 746. https://doi.org/10.3390/jpm12050746.
Xie, Gengqiang et al. Genomic variations drive phenotypic heterogeneity in pancreatic cancer cells. Cold Spring Harbor Laboratory 2022.
Cavo, Marta et al. A Synergic Approach to Enhance Long-term Culture and Manipulation of MiaPaCa Pancreatic Cancer Spheroids. Scientific Reports 2020, 10:10192.
Gradiz, Rui et al. MIA PaCa-2 and PANC-1—Pancreas Ductal Adenocarcinoma Cell Lines with Neuroendocrine Differentiation and Somatostatin Receptors. Scientific Reports 2016, 6:21648.
El Amrani, Mehdi et al. Gemcitabine-Induced Epithelial-Mesenchymal Tranition-like Changes Sustain Chemoresistance of Pancreatic Cancer Cells of Mesenchymal-like Phenotype. Molecular Carcinogenesis 2019, 58:1985-1997.

* cited by examiner

*Primary Examiner* — Marcela M Cordero Garcia
(74) *Attorney, Agent, or Firm* — Michele L. Lawson; Smith & Hopen, P.A.

(57) ABSTRACT

Novel compounds and methods of using the compounds and compositions to treat pancreatic cancer are presented. Novel compounds N-(5-fluoro-2-oxo-1-(tetrahydrofuran-2-yl)-1,2-dihydropyrimidin-4-yl)octanamide and N-(5-fluoro-2-oxo-1-(tetrahydrofuran-2-yl)-1,2-dihydropyrimidin-4-yl)dodecanamide are provided. The compounds have been shown to induce cytotoxicity in pancreatic cancer cells and can serve as a novel oral treatment for pancreatic cancer.

10 Claims, 16 Drawing Sheets

PYRIMIDINE NUCLEOSIDES AS ANTICANCER AGENTS AGAINST PANCREATIC CANCER

CROSS REFERENCE TO RELATED APPLICATIONS

This application is a nonprovisional of and claims priority to U.S. Provisional Patent Application Ser. No. 63/188,563, entitled "Novel Pyrimidine Nucleosides as Anticancer Agents Against Pancreatic Cancer", filed May 14, 2021, the contents of which are hereby incorporated by reference into this disclosure.

FIELD OF INVENTION

This invention relates to compounds and methods of treatment for cancer. Specifically, the invention provides novel compounds and methods of treatment for pancreatic cancer.

BACKGROUND OF THE INVENTION

Pancreatic cancer (PC) is a deadly disease that is mostly diagnosed at an incurable stage. The American Cancer Society estimated an incidence of 57,600 cases of PC for the year 2020, with 47,050 deaths, making it the third most deadly cancer in the United States. About 90% of PCs are diagnosed at advanced stage, where surgical resection offering best prognosis, is ineffective. Chemotherapy then becomes the main standardized treatment. However, this comes with high toxicities and drug resistance that greatly contributed to a less than 5% survival rate within 5 years of diagnosis.

In light of the limited treatment options for pancreatic cancer, what is needed is a novel pancreatic cancer treatment with limited side effects, lower toxicity to the patient as compared to current therapies, an elevated therapeutic index, and improved patient response rate.

SUMMARY OF INVENTION

The inventors have discovered novel fluoropyrimidine nucleosides and detail the drug design, drug synthesis, and cell viability studies against pancreatic cancer as well as other cancer cell lines herein. The strategy of using a prodrug to deliver the 5-fluorouracil (5-FU) to target cancer represents a state of art challenge needing comprehensive knowledge of medicinal chemistry, organic synthesis, and biopharmaceuticals.

The well-defined prodrug fluoropyrimidine nucleosides, in which the structural features are responsible for oral availability, cytotoxicity, toxicity, and efficacy against the cancer cell lines, have two modifications compared with parent molecule 5-FU: 1) a tetrahydrofuran ring C-1 position, and 2) an amide or a carbamate chain at C-4 position. New drugs are orally available which avoids the damage to intestinal mucosa by first-pass metabolism, reduces toxicity to a maximum extent, and reduces side effects in the GI tract. The new drugs have a prolonged half-life and keep lower peak concentration of 5-FU in blood stream which lowers the toxicity, elevates the therapeutic index, improves patient response rate, and reduces the side effects.

The prodrug fluoropyrimidine nucleosides have improved potency, efficacy, selectivity, and an improved drug resistance profile. The new compounds also provide an alternative for clinical therapeutics as a front line drug.

In an embodiment, a composition is presented comprising Formula (I):

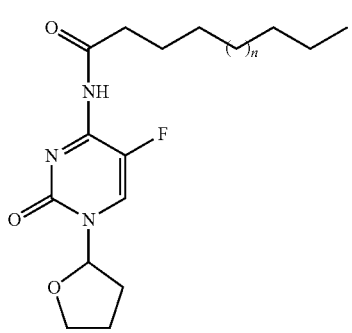

wherein n is an integer from 1 to 5.

The composition may further comprise a pharmaceutically acceptable carrier. In some embodiments, n is 1 or 5.

In another embodiment, a method of inducing cytotoxicity in cancer cells is presented comprising administering to the cancer cells a therapeutically effective amount of a composition comprising Formula (I):

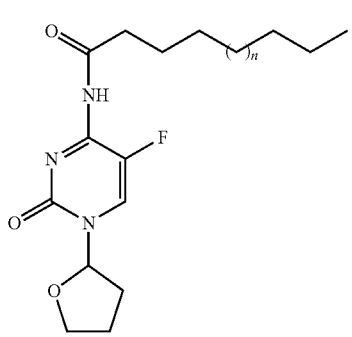

wherein n is an integer from 1 to 5 and a pharmaceutically acceptable carrier. The administration of the therapeutically effective amount of the composition induces cytotoxicity in the cancer cells thus reducing an amount of the cancer cells. In some embodiments, n is 1 or 5 and the cancer is pancreatic cancer.

In a further embodiment, a method of treating pancreatic cancer in a patient in need thereof is presented comprising administering to the patient a therapeutically effective amount of a composition comprising

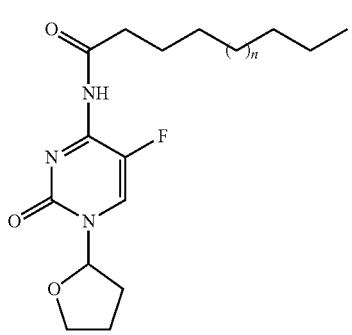

wherein n is an integer from 1 to 5 and a pharmaceutically acceptable carrier. The administration of the therapeutically effective amount of the composition induces cytotoxicity in the pancreatic cancer cells to treat the pancreatic cancer. In some embodiments, n is 1 or 5.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
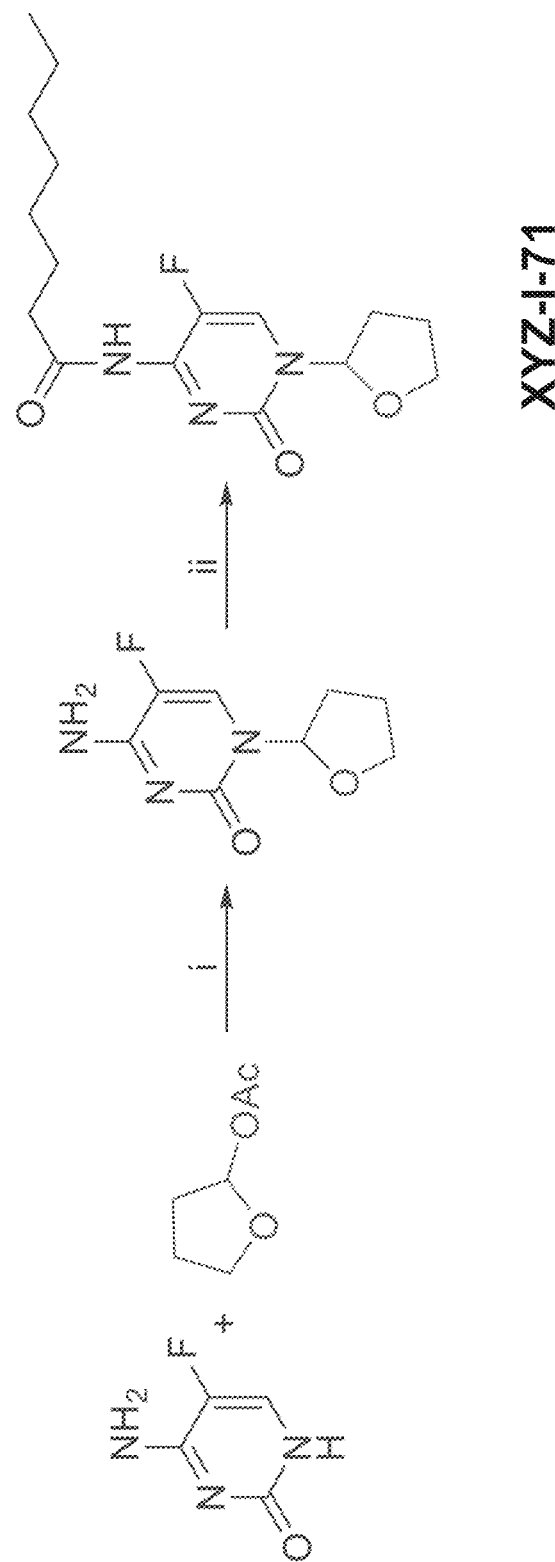
FIG. 1 is an image depicting Scheme I for synthesizing XYZ-I-71 (Compound I).

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

As used herein, the singular forms "a," "an" and "the" include plural referents unless the context clearly dictates otherwise.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

As used herein, "about" means approximately or nearly and in the context of a numerical value or range set forth means±10% of the numerical.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein "patient" is used to describe an animal, preferably a human, to whom treatment is administered, including prophylactic treatment with the compositions of the present invention. "Patient" is used interchangeably with "subject" herein.

As used herein "animal" means a multicellular, eukaryotic organism classified in the kingdom Animalia or Metazoa. The term includes, but is not limited to, mammals. Non-limiting examples include humans, rodents, mammals, aquatic mammals, domestic animals such as dogs and cats, farm animals such as sheep, pigs, cows and horses. Wherein the terms "animal" or the plural "animals" are used, it is contemplated that it also applies to any animals.

As used herein, the term "pharmaceutically acceptable carrier" is used to describe any of the standard pharmaceutically acceptable carriers. The pharmaceutically acceptable carrier can include excipients such as diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, 19' ed.) describes formulations which can be used in connection with the subject invention.

Any of the compounds disclosed herein may be administered with or without an excipient. Excipients include, for example, encapsulating materials or additives such as absorption accelerators; antioxidants; binders; buffers; coating agents; coloring agents; diluents; disintegrating agents; emulsifiers; extenders; fillers; flavoring agents; humectants; lubricants; perfumes; preservatives; propellants; releasing agents; sterilizing agents; sweeteners; solubilizers; wetting agents; and mixtures thereof.

As used herein, "administering" or "administration" refers to the process by which the compounds of the present invention are delivered to a subject. The compounds of the present invention may be administered in a variety of ways including, but not limited to, bucally, orally, or parenterally (intramuscularly, intraperitoneally, intrasternally, intravenously, subcutaneously). Any of the compounds may also be delivered through encapsulation in vesicles such as liposomes, niosomes, micelles, etc.

"Treatment" or "treating" as used herein refers to any of: the alleviation, amelioration, elimination and/or stabilization of a symptom or characteristic, as well as delay in progression of a symptom of a particular disorder. For example, "treatment" of cancer may include any one or more of the following: amelioration and/or elimination of one or more symptoms/characteristics associated with cancer, reduction of one or more symptoms/characteristics of cancer, stabilization of symptoms/characteristics of cancer, and delay in progression of one or more symptoms/characteristics of cancer.

As used herein, the term "therapeutically effective amount" is determined based on such considerations as known in the art including the recipient of the treatment, the recipient's tolerance for the compound, the disorder being treated, the severity of the disorder being treated, the composition containing the compound, the time of administration, the route of administration, the duration of treatment, the potency of the compound, the bioavailability of the compound, the rate of clearance of the compound from the body, and whether or not another active agent is co-administered. The amount of the compound of the instant invention that may be administered to a subject must be effective to achieve a response, including but not limited to, improved survival rate, more rapid recovery, and improvement or elimination of symptoms associated with cancers. In accordance with the present invention, a suitable single dose size is a dose that is capable of preventing or alleviating (reducing or eliminating) a symptom in a patient when administered one or more times over a suitable time period. One of ordinary skill in the art can readily determine appropriate single dose sizes for systemic administration based on the size of a mammal and the route of administration.

The term "cancer" as used herein refers to any malignant neoplastic condition involving unregulated cell growth. Non-limiting examples of a cancer that can be treated with the intended use described herein include, but are not limited to, the following: pancreatic cancer such as, but not limited to, insulinoma, gastrinoma, glucagonoma, vipoma, somatostatin-secreting tumor, and carcinoid or islet cell tumor; leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's lymphoma, non-Hodgkin's lymphoma; multiple myelomas such as but not limited to smoldering multiple myeloma, nonsecretory myeloma, osteosclerotic myeloma, placancer cell leukemia, solitary placancercytoma and extramedullary placancercytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; glial brain tumors (i.e., gliomas) such as but not limited to, astrocytoma, ependymoma, oligodendroglioma, brain stem glioma, optic glioma, diffuse intrinsic pontine glioma, mixed glioma (i.e., oligoastrocytoma), glioblastoma, glioblastoma multiforme, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (cancer cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, placancercytoma, verrucous carcinoma, and oat cell (cancer cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., *J. B. Lippincott Co.*, Philadelphia and Murphy et al., 1997, *Informed Decisions: The Complete Book of Cancer Diagnosis, Treatment, and Recovery*, Viking Penguin, Penguin Books U.S.A., Inc., United States of America). In some embodiments, the cancer is pancreatic cancer.

The term "compound" as used herein refers to a chemical formulation, either organic or inorganic, which induces a desired pharmacological and/or physiological effect on a subject when administered in a therapeutically effective amount. "Compound" is used interchangeably herein with "drug" and "therapeutic agent". When the compound name disclosed herein conflicts with the structure depicted, the structure shown will supercede the use of the name to define the compound intended.

As used herein, the term "substituent" means positional variables on the atoms of a core molecule that are attached at a designated atom position, replacing one or more hydrogen atoms on the designated atom, provided that the atom of attachment does not exceed the available valence or shared valence, such that the substitution results in a stable compound. Accordingly, combinations of substituents and/or variables are permissible only if such combinations result in stable compounds. Any carbon atom as well as heteroatom with a valence level that appears to be unsatisfied as described or shown herein is assumed to have a sufficient number of hydrogen atom(s) to satisfy the valences described or shown.

For the purposes of this description, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may be attached more than once on the structure of a core molecule, where the pattern of substitution at each occurrence is independent of the pattern at any other occurrence. Further, the use of a generic substituent variable on a core structure for a compound described herein is understood to include the replacement of the generic substituent with specie substituents that are included within the particular genus, e.g., aryl may be replaced with phenyl or naphthalenyl and the like, such that the resulting compound is to be included within the scope of the compounds described herein.

As used herein, the term "optionally substituted" means that the specified substituent variables, groups, radicals or moieties represent the scope of the genus and may be independently chosen as needed to replace one or more hydrogen atoms on the designated atom of attachment of a core molecule.

As used herein, the terms "stable compound" or "stable structure" mean a compound that is sufficiently robust to be isolated to a useful degree of purity from a reaction mixture and formulations thereof into an efficacious therapeutic agent.

As used herein, the term "form" means a compound of Formula (I) selected from a free acid, free base, salt, ester, hydrate, solvate, chelate, clathrate, polymorph, isotopologue, stereoisomer, racemate, enantiomer, diastereomer, or tautomer thereof.

As used herein, the term "prodrug" means that a functional group on a compound of Formula (I) is in a form (e.g., acting as an active or inactive drug precursor) that is transformed in vivo to yield an active or more active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by V. J. Stella, et. al., "Biotechnology: Pharmaceutical Aspects, Prodrugs: Challenges and Rewards," American Association of Pharmaceutical Scientists and Springer Press, 2007.

The compounds of Formula (I) or a form thereof can form salts, which are intended to be included within the scope of this description. Reference to a compound of Formula (I) or a form thereof herein is understood to include reference to salts thereof, unless otherwise indicated. The term "salt(s)", as employed herein, denotes acidic salts formed with inorganic and/or organic acids, as well as basic salts formed with inorganic and/or organic bases.

The term "pharmaceutically acceptable salt(s)", as used herein, means those salts of compounds of Formula (I) or a form thereof described herein that are safe and effective (i.e., non-toxic, physiologically acceptable) for use in mammals and that possess biological activity, although other salts are also useful. All such acid salts and base salts are intended to be included within the scope of pharmaceutically acceptable salts as described herein. In addition, all such acid and base salts are considered equivalent to the free forms of the corresponding compounds for purposes of this description.

The use of the terms "salt," "solvate," "ester," "prodrug" and the like, is intended to apply equally to the salt, solvate, ester and prodrug of enantiomers, stereoisomers, rotamers, tautomers, positional isomers, racemates, isotopologues or prodrugs of the instant compounds.

Unless otherwise stated, structures depicted herein are also meant to include all isomeric (e.g., enantiomeric, diastereomeric, optical, and geometric (or conformational)) forms of the structure or a form thereof (including salts, solvates, esters, and prodrugs and transformed prodrugs thereof); for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms.

The compounds of Formula (I) or a form thereof described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds of Formula (I) or a form thereof described herein are (S) isomers and may exist as enantiomerically pure compositions substantially comprising only the (S) isomer. In another embodiment, the compounds of Formula (I) or a form thereof described herein are (R) isomers and may exist as enantiomerically pure compositions substantially comprising only the (R) isomer. As one of skill in the art will recognize, when more than one chiral center is present, the compounds of Formula (I) or a form thereof described herein may also exist as a (R,R), (R,S), (S,R) or (S,S) isomer, as defined by IUPAC Nomenclature Recommendations.

As used herein, the term "substantially pure" refers to compounds of Formula (I) or a form thereof consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

As used herein, the term "racemate" refers to any mixture of isometric forms that are not "enantiomerically pure", including mixtures such as, without limitation, in a ratio of about 50/50, about 60/40, about 70/30, or about 80/20, about 85/15 or about 90/10.

All stereoisomers (for example, geometric isomers, optical isomers and the like) of the present compounds of Formula (I) or a form thereof (including salts, solvates, esters and prodrugs and transformed prodrugs thereof), which may exist due to asymmetric carbons on various substituents, including enantiomeric forms (which may exist even in the absence of asymmetric carbons), rotameric forms, atropisomers, diastereomeric and regioisomeric forms, are contemplated within the scope of the description herein. Individual stereoisomers of the compounds of Formula (I) or a form thereof described herein may, for example, be substantially free of other isomers, or may be present in a racemic mixture, as described supra.

The term "isotopologue" refers to isotopically-enriched compounds of Formula (I) or a form thereof which are identical to those recited herein, but for the fact that one or more atoms are replaced by an atom having an atomic mass or mass number different from the atomic mass or mass number usually found in nature.

One or more compounds of Formula (I) or a form thereof described herein may exist in unsolvated as well as solvated forms with pharmaceutically acceptable solvents such as water, ethanol, and the like, and the description herein is intended to embrace both solvated and unsolvated forms As used herein, the term "solvate" means a physical association of a compound of Formula (I) or a form thereof described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates.

Polymorphic crystalline and amorphous forms of the compounds of Formula (I) or a form thereof, and of the salts, solvates, esters and prodrugs of the compounds of Formula (I) or a form thereof, are further intended to be included in the scope of the compounds of Formula (I) or a form thereof described herein.

Also falling within the scope described herein are the in vivo metabolic products of the compounds of Formula (I) or a form thereof. Such products may result, for example, from the oxidation, reduction, hydrolysis, amidation, glucuronidation, esterification and the like of the administered compound of Formula (I) or a form thereof, primarily due to enzymatic processes. Accordingly, the compounds of Formula (I) or a form thereof described herein include those produced by a process comprising contacting a compound of Formula (I) or a form thereof described herein with a mammalian tissue or a mammal for a period of time sufficient to yield a metabolic product thereof.

The inventors have developed novel forms of fluoropyrimidine nucleosides as compounds for treatment of cancer, specifically pancreatic cancer. The well-defined prodrug fluoropyrimidine nucleosides, in which the structural features are responsible for oral availability, cytotoxicity, toxicity, and efficacy against the cancer cell lines, have two modifications compared with parent molecule 5-FU: 1) a tetrahydrofuran ring C-1 position, and 2) an amide or a carbamate chain at C-4 position. New drugs are orally available which avoids the damage to intestinal mucosa by first-pass metabolism, reduces toxicity to a maximum extent, and reduces side effects in the GI tract. The new drugs have a prolonged half-life and keep lower peak concentration of 5-FU in blood stream which lowers the toxicity, elevates the therapeutic index, improves patient response rate, and reduces the side effects.

The following non-limiting examples illustrate exemplary compounds and methods thereof in accordance with various embodiments of the disclosure. The examples are merely illustrative and are not intended to limit the disclosure in any way.

Example 1—Synthesis of Compound I (XYZ-I-71 aka XYZ-71)

Compound I was synthesized according to Scheme I as depicted in FIG. 1. A mixture of 5-fluorocytosine (2.0 g, 15.50 mmol), tetrahydrofuran-2-yl acetate (4.2 g, 32.31 mmol), 1,8-Diazabicyclo[5.4.0]undec-7-ene (DBU) (5.0 g, 32.89 mmol) in pyridine (20 mL) was heated with stirring at 95° C. for 48 hrs in a sealed flask. After cooling to room temperature, the reaction was diluted with EtOAc (400 mL) and washed with water (300×2 mL). The aqueous was collected and concentrated in vacuo to dryness. The residue was dried under vacuum for 48 hrs and followed by crystallization (MeOH/EtOAc/Hexane) to give 4-amino-5-fluoro-1-(tetrahydrofuran-2-yl)pyrimidin-2(1H)-one, 2.25 g, in a yield of 73%.

NMR Data of 4-amino-5-fluoro-1-(tetrahydrofuran-2-yl) pyrimidin-2(1H)-one (Intermediate Compound)

$^1$H NMR (DMSO-d$^6$, 300 MHz) δ 7.71 (1H, d, J=7.2 Hz), 7.66 (1H, brs), 7.42 (1H, brs), 5.81-5.84 (1H, m), 4.20 (1H, dd, J=5.7, 12.9 Hz), 3.76 (1H, dd, J=7.2, 12.9 Hz), 2.10-2.21 (1H, m), 1.80-1.94 (3H, m).

$^{13}$C NMR (DMSO-d$^6$, 151 MHz) δ 157.9 (d, J=13.2 Hz), 153.8, 136.5 (d, J=240.6 Hz), 125.7 (d, J=31.2 Hz), 87.1, 69.6, 32.5, 23.9.

To a solution of 4-amino-5-fluoro-1-(tetrahydrofuran-2-yl)pyrimidin-2(1H)-one (1.0 g, 5.02 mmol) in pyridine (10 mL) was added while stirring a solution of octanoyl chloride (1 g, 6.15 mmol) in CH$_2$Cl$_2$ (5 mL) in dropwise at 0° C. in 30 min. The solution was stirred at room temperature for 12 hrs. The reaction was diluted with EtOAc (300 mL) and followed by washing with saturated. NaHCO$_3$ (100 mL), brine (100 mL). The organic layer was dried with Na$_2$SO$_4$, filtered, and concentrated in vacuo to dryness. The residue was purified on silica gel on Isolera chromatograph with gradient eluant (Hexane/EtOAc). After crystallization from EtOAc/Hexane, N-(5-fluoro-2-oxo-1-(tetrahydrofuran-2-yl)-1,2-dihydropyrimidin-4-yl)octanamide was obtained, 1.22 g, in a yield of 74%.

Log P: 2.27; Rf (Hexane/EtOAc, 1/3): 0.30; MP (melting point): 119-120° C.; Purity is greater than 99.6%

NMR Data for N-(5-fluoro-2-oxo-1-(tetrahydrofuran-2-yl)-1,2-dihydropyrimidin-4-yl)octanamide (XYZ-I-71)

$^1$H NMR (CDCl$_3$, 300 MHz) δ 7.80 (1H, brs), 7.67 (1H, d, J=6.0 Hz), 5.94 (1H, dd, J=1.5, 5.1 Hz), 4.24 (1H, dt, J=3.9, 8.1 Hz), 4.04 (1H, q, J=7.8 Hz), 2.97 (2H, brs), 2.43-2.55 (1H, m), 2.08-2.18 (1H, m), 2.00-2.05 (1H, m), 1.78-1.89 (1H, m), 1.63-1.73 (2H, m), 1.22-1.38 (8H, m), 0.87 (3H, t, J=6.9 Hz).

$^{13}$C NMR (CDCl$_3$, 151 MHz) δ 174.6, 152.9 (d, J=12.4 Hz), 152.2, 136.8 (d, J=245.8 Hz), 127.6 (d, J=31.4 Hz), 88.8, 70.5, 38.0, 33.0, 31.6, 29.0, 28.9, 24.6, 23.4, 22.5, 14.0.

TABLE 1

Elemental analysis of XYZ-71

| Element | Theory | Found |
|---|---|---|
| C | 59.06 | 58.95 |
| H | 7.43 | 7.34 |
| N | 12.91 | 12.82 |

Calcd for C$_{16}$H$_{24}$FN$_3$O$_3$: C, 59.06; H, 7.43; N, 12.91. Found: C, 58.95; H, 7.34; N, 12.82. Molecular weight: 325.38, Log P: 2.27. Purity is greater than 99.6% based on the calculation of elemental analysis.

Purity and Molecular Mass of XYZ-71

Figure 2:
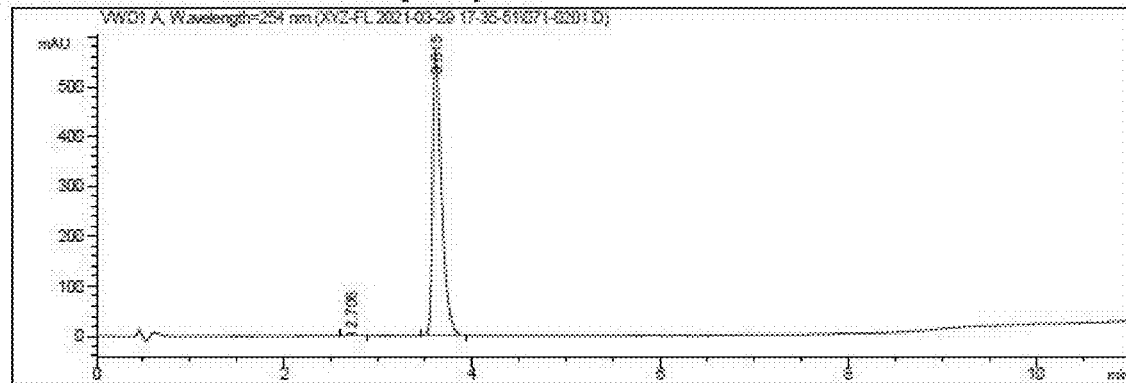
FIG. 2 is an image of a chromatogram depicting the purity of XYZ-71. The results obtained from the chromatogram indicate that XYZ-71 has a higher percent of purity with little to no impurities.

As shown in FIG. 2, the purity of XYZ-71 was determined using high-performance liquid chromatography in tandem with a UV/VIS detector at 254 nm wavelength. HPLC analysis confirms the identity of the XYZ-71 and quantifies the purity of the compound. The peak purity of XYZ-71 was evaluated by comparing it with gemcitabine (Gem) as a reference standard. Analog XYZ-71 chromatogram showed a purity of 99.1% separated at a wavelength of 254 nm. The results obtained from the chromatogram indicate that XYZ-71 has a higher percent of purity with little to no impurities.

Figure 3:
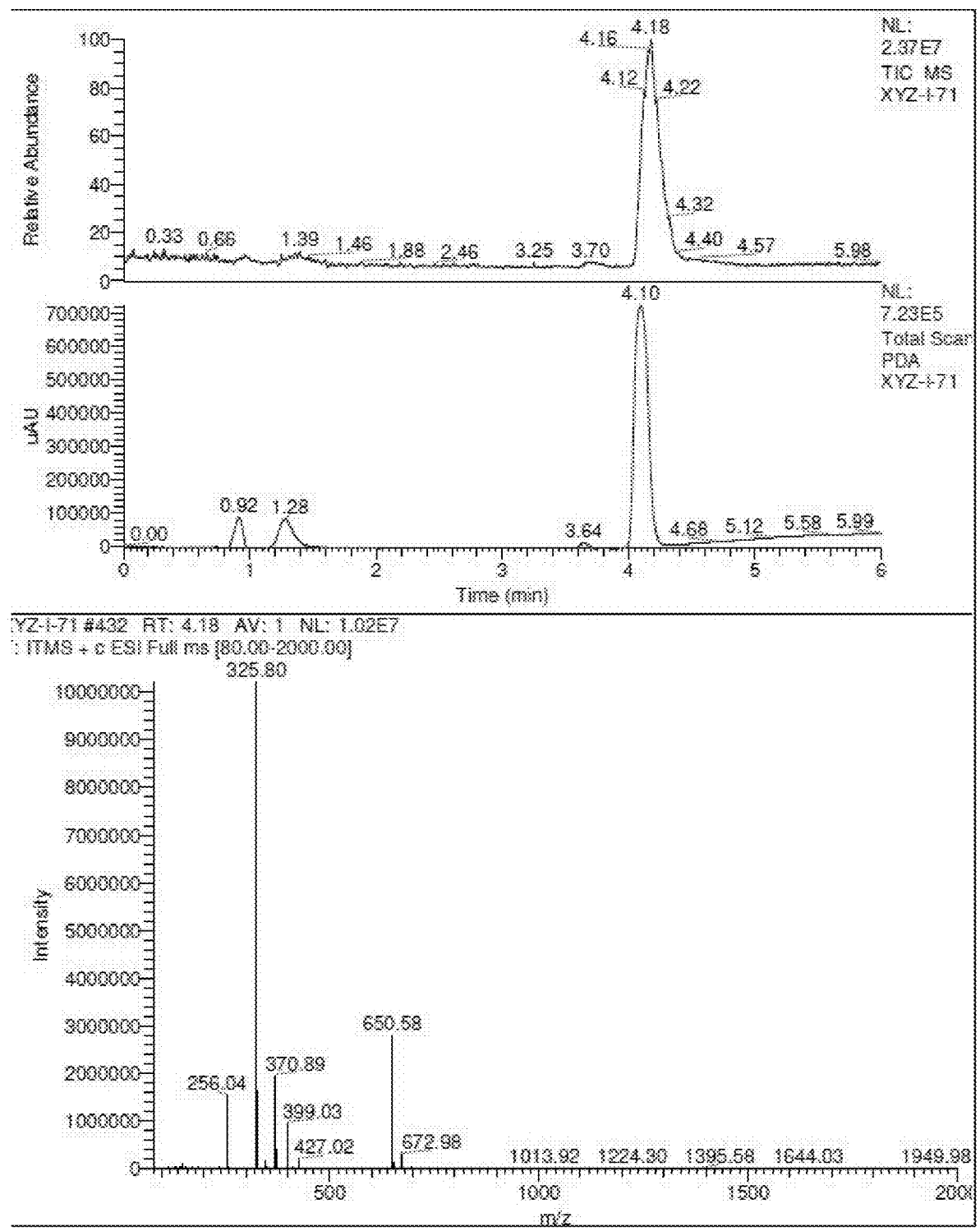
FIG. 3 is an image depicting the molecular mass of ions of XYZ-71. Mass spectrometry was used to measure the precise molecular mass of ions constituent of XYZ-71 determined by their mass-to-charge ratio (m/z). The Electrospray ionization (ESI) method was used in tandem with HPLC to determine the molecular mass of XYZ-71. The mass spectrum of XYZ-71 showed a ratio peak of 325.80 m/z.

As shown in FIG. 3, mass spectrometry was used to measure the precise molecular mass of ions constituent of XYZ-71 determined by their mass-to-charge ratio (m/z). The Electrospray ionization (ESI) method was used in tandem with HPLC to determine the molecular mass of XYZ-71. The mass spectrum of XYZ-71 showed a ratio peak of 325.80 m/z.

Example 2—Synthesis of Compound I (XYZ-I-73 aka XYZ-73)

Figure 4:
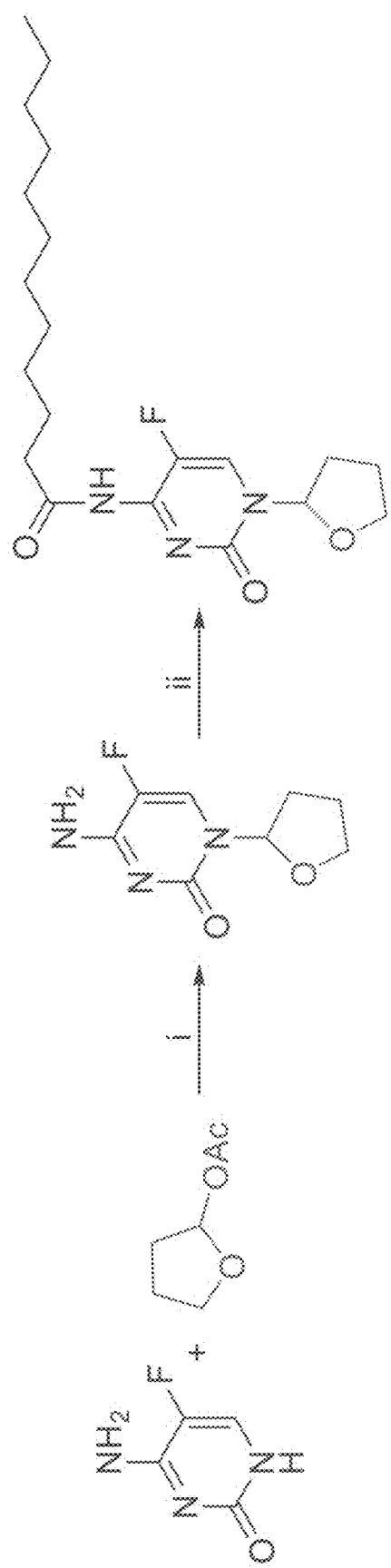
FIG. 4 is an image depicting Scheme II for synthesizing XYZ-I-73 (Compound II).

Compound II was synthesized according to Scheme II as depicted in FIG. 4. A mixture of 5-fluorocytosine (2.0 g, 15.50 mmol), tetrahydrofuran-2-yl acetate (4.2 g, 32.31 mmol), 1,8-Diazabicyclo[5.4.0]undec-7-ene (DBU) (5.0 g, 32.89 mmol) in pyridine (20 mL) was heated with stirring at 95° C. for 48 hrs in a sealed flask. After cooling to room temperature, the reaction was diluted with EtOAc (400 mL) and washed with water (300×2 mL). The aqueous was collected and concentrated in vacuo to dryness. The residue was dried under vacuum for 48 hrs and followed by crystallization (MeOH/EtOAc/Hexane) to give 4-amino-5-fluoro-1-(tetrahydrofuran-2-yl)pyrimidin-2(1H)-one, 2.25 g, in a yield of 73%.

NMR Data of 4-amino-5-fluoro-1-(tetrahydrofuran-2-yl) pyrimidin-2(1H)-one (Intermediate Compound)

$^1$H NMR (DMSO-d$^6$, 300 MHz) δ 7.71 (1H, d, J=7.2 Hz), 7.66 (1H, brs), 7.42 (1H, brs), 5.81-5.84 (1H, m), 4.20 (1H, dd, J=5.7, 12.9 Hz), 3.76 (1H, dd, J=7.2, 12.9 Hz), 2.10-2.21 (1H, m), 1.80-1.94 (3H, m).

$^{13}$C NMR (DMSO-d$^6$, 151 MHz) δ 157.9 (d, J=13.2 Hz), 153.8, 136.5 (d, J=240.6 Hz), 125.7 (d, J=31.2 Hz), 87.1, 69.6, 32.5, 23.9.

To a solution of 4-amino-5-fluoro-1-(tetrahydrofuran-2-yl)pyrimidin-2(1H)-one (1.0 g, 5.02 mmol) in pyridine (10 mL) was added with stirring a solution of lauroyl chloride (1.31 g, 6.03 mmol) in CH$_2$Cl$_2$ (5 mL) in dropwise at 0° C. in 30 min. The solution was stirred at room temperature for 12 hrs. The reaction was diluted with EtOAc (300 mL) and followed by washing with sat. NaHCO$_3$ (100 mL), brine (100 mL). The organic layer was dried with Na$_2$SO$_4$, filtered, and concentrated in vacuo to dryness. The residue was purified on silica gel on Isolera chromatograph with gradient eluant (Hexane/EtOAc). After crystallization from EtOAc/Hexane, yielded N-(5-fluoro-2-oxo-1-(tetrahydrofuran-2-yl)-1,2-dihydropyrimidin-4-yl)dodecanamide, 1.34 g, in a yield of 70%. Log P: 3.94; Rf (Hexane/EtOAc, 1/3): 0.32.; MP (melting point): 107-108° C., Purity is greater than 99.6%.

NMR Data for XYZ-I-73

$^1$H NMR (CDCl$_3$, 300 MHz) δ 7.73 (1H, brs), 7.67 (1H, d, J=5.4 Hz), 5.94 (1H, dd, J=1.5, 5.1 Hz), 4.24 (1H, dt, J=3.9, 7.5 Hz), 4.02 (1H, q, J=8.7 Hz), 2.99 (2H, brs), 2.42-2.56 (1H, m), 2.10-2.19 (1H, m), 2.00-2.07 (1H, m), 1.79-1.89 (1H, m), 1.66-1.73 (2H, m), 1.18-1.38 (16H, m), 0.87 (3H, t, J=6.9 Hz).

$^{13}$C NMR (CDCl$_3$, 151 MHz) δ 174.19, 152.91 (d, J=13.8 Hz), 152.46, 156.73 (d, J=244.9 Hz), 127.65 (d, J=31.6 Hz), 88.76, 70.54, 37.98, 33.01, 31.84, 29.56, 29.44, 29.41, 29.27, 29.04, 24.46, 23.41, 22.61, 14.04.

TABLE 2

Elemental Analysis of XYZ-I-73

| Element | Theory | Found |
|---|---|---|
| C | 62.97 | 62.77 |
| H | 8.46 | 8.51 |
| N | 11.01 | 10.83 |

Calcd for C$_{20}$H$_{32}$FN$_3$O$_3$: C, 62.97; H, 8.46; N, 11.01. Found: C, 62.77; H, 8.51; N, 10.83. Purity is greater than 99.6%. Molecular weight: 381.49, Log P: 3.94.

Purity and Molecular Mass of XYZ-I-73

Figure 5:
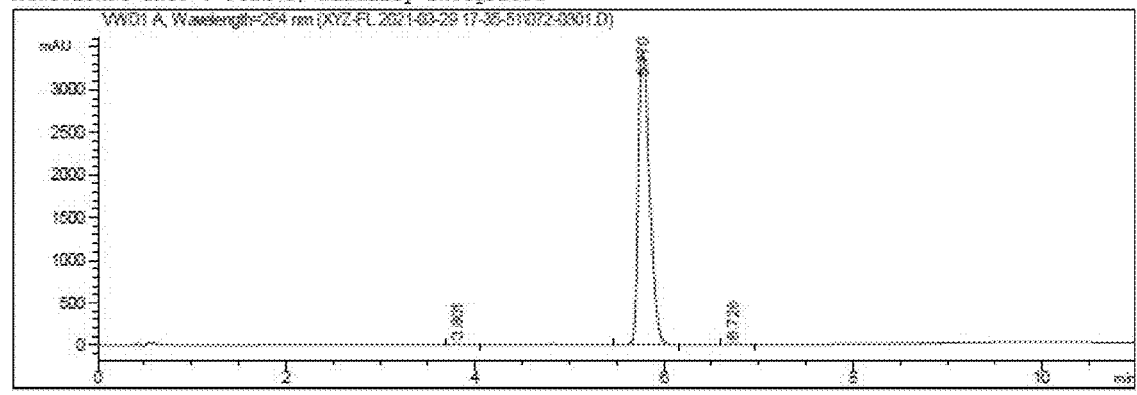
FIG. 5 is an image of a chromatogram depicting the purity of XYZ-73. The results obtained from the chromatogram indicate that XYZ-73 has a higher percent of purity with little to no impurities.

As shown in FIG. 5, the purity of XYZ-73 was determined using high-performance liquid chromatography in tandem with a UV/VIS detector at 254 nm wavelength. HPLC analysis confirms the identity of the XYZ-73 and quantifies the purity of the compound. The peak purity of XYZ-73 was evaluated by comparing it with gemcitabine (Gem) as a reference standard. XYZ-73 Chromatogram showed a purity of 99.5% separated at a wavelength of 254 nm. The results obtained from the chromatogram indicate that XYZ-73 has a higher percent of purity with little to no impurities.

Figure 6:
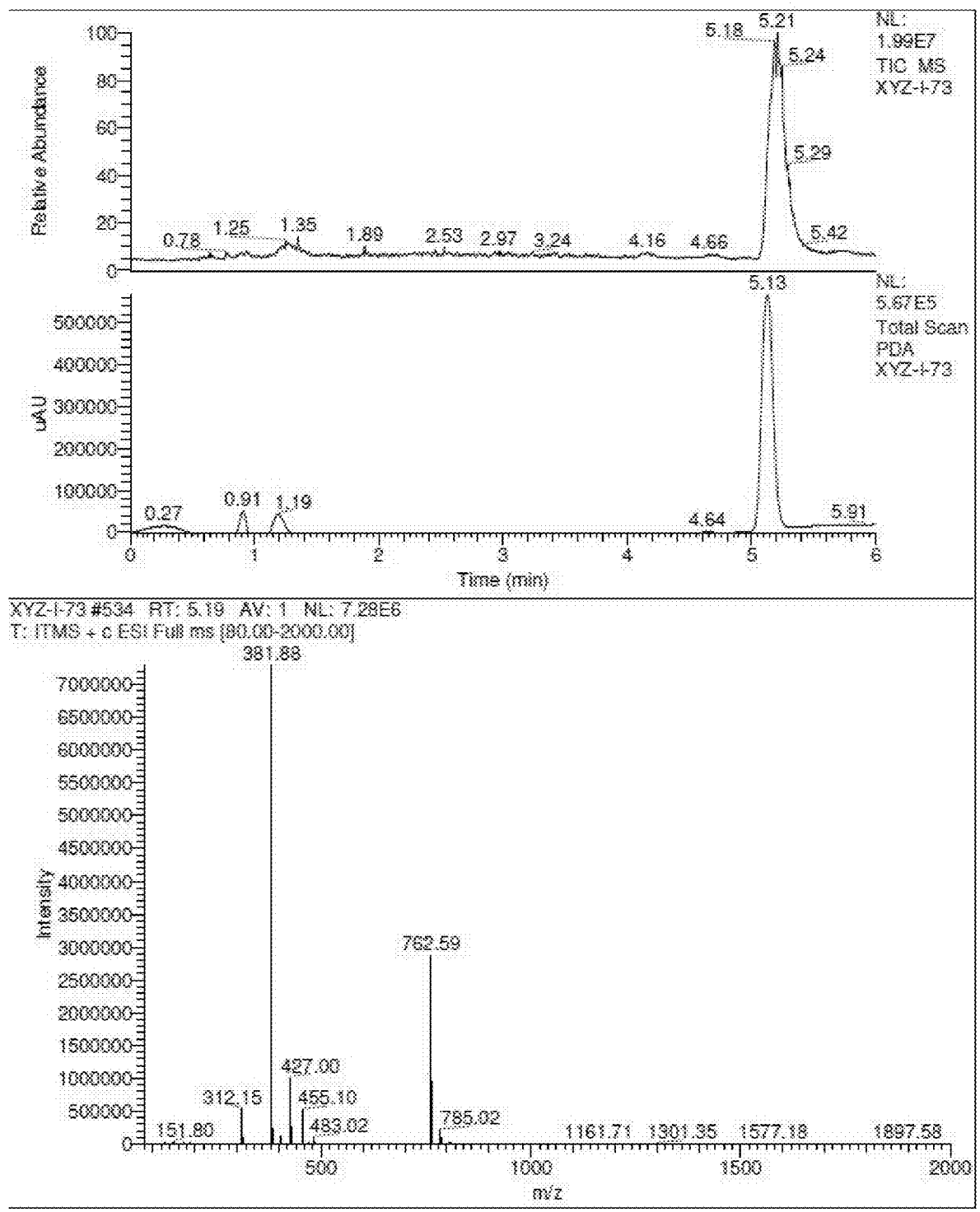
FIG. 6 is an image depicting the molecular mass of ions of XYZ-73. Mass spectrometry was used to measure the precise molecular mass of ions constituent of XYZ-73 determined by their mass-to-charge ratio (m/z). The Electrospray ionization (ESI) method was used in tandem with HPLC to determine the molecular mass of XYZ-73. The mass spectrum of XYZ-73 showed a ratio peak of 381.88 m/z.

As shown in FIG. 6, mass spectrometry was used to measure the precise molecular mass of ions constituent of XYZ-73 determined by their mass-to-charge ratio (m/z). The Electrospray ionization (ESI) method was used in tandem with HPLC to determine the molecular mass of XYZ-73. The mass spectrum of XYZ-73 showed a ratio peak of 381.88 m/z.

Example 3—In Vitro Cell Viability Studies—Testing the Efficacy of Compounds XYZ-I-71 and XYZ-I-73 Against MiaPaCa-2 Pancreatic Cancer Cell Line Prior to viability studies, Dulbecco's modified Eagle medium (DMEM) with high glucose and L-glutamine was supplemented with 10% fetal bovine serum (FBS) and 1% penicillin-streptomycin (PenStrep). Briefly, MiaPaCa-2 cells were seeded at a density of 1×10$^3$ per well in 96-well plates in triplicates for each drug concentration level and incubated at 5% CO$_2$ and temperature of 37° C. At 70-75% confluence, MiaPaCa-2 cells were treated with compounds XYZ-I-71, XYZ-I-73, 5-Fluorouracil (5-FU), Gemcitabine (Gem) and Irinotecan. Varying concentrations of 4NSG was prepared from its stock solution with growth medium. For 5-Fluorouracil (5-FU), Gemcitabine Hydrochloride (GemHCl) and Irinotecan, a stock solution was prepared with phosphate-buffered saline (PBS) and serially diluted with growth medium to prepare varied concentrations: thus 3, 6, 12, 25, and 100 μM. Cells was treated with 100 μL of each drug concentration in triplicates and incubated for 48 hr. At termination, 20 μL of 0.05% resazurin sodium salt (Alamar Blue®) was added and incubated at optimum conditions (5% CO$_2$, 37° C.) for 4 hr. Fluorimetric analysis was determined at excitation wavelength of 560/580 nm and emission wavelength of 590/610 nm and the percent viable cells per concentration was calculated. For statistical analysis, results are presented as mean±SD. Data were analyzed for significance by one-way ANOVA, using GraphPad Prism 5 Software and IC$_{50}$ values were determined.

Figure 7:
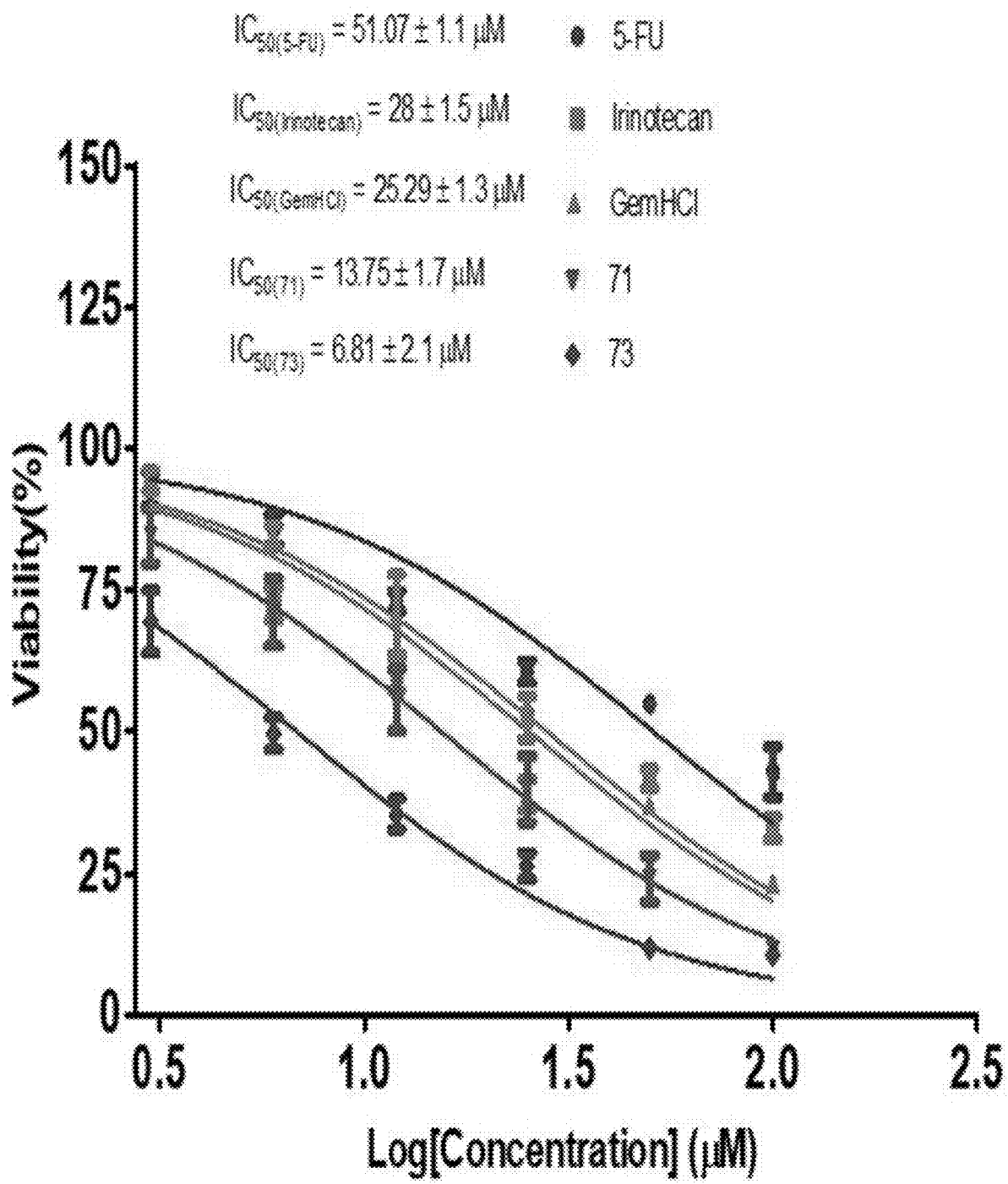
FIG. 7 is a graph depicting the cytotoxicity of XYZ-I-71, XYZ-I-73, 5-FU, Irinotecan, and Gemcitabine hydrochloride (GemHCl) against MiaPaCa-2 cancer cells.
Figure 8:
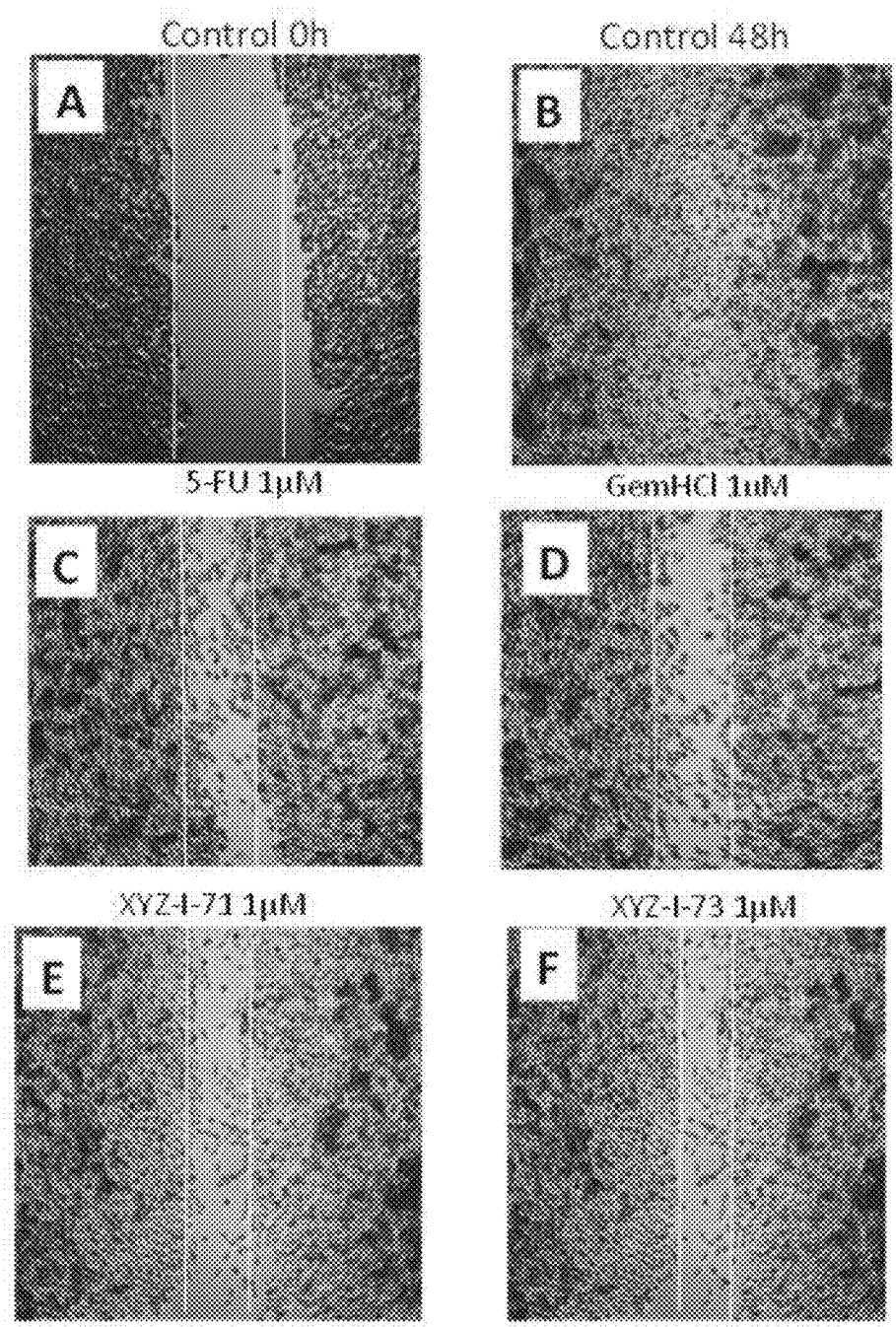
FIG. 8A-F are a series of images depicting migration studies of (A) Control at 0 h; (B) Control at 48 h; (C) 5-FU; (D) GemHCl; (E) XYZ-I-71; and (F) XYZ-I-73 on MiaPaCa-2 cells at 1 µM concentration.
Figure 9:
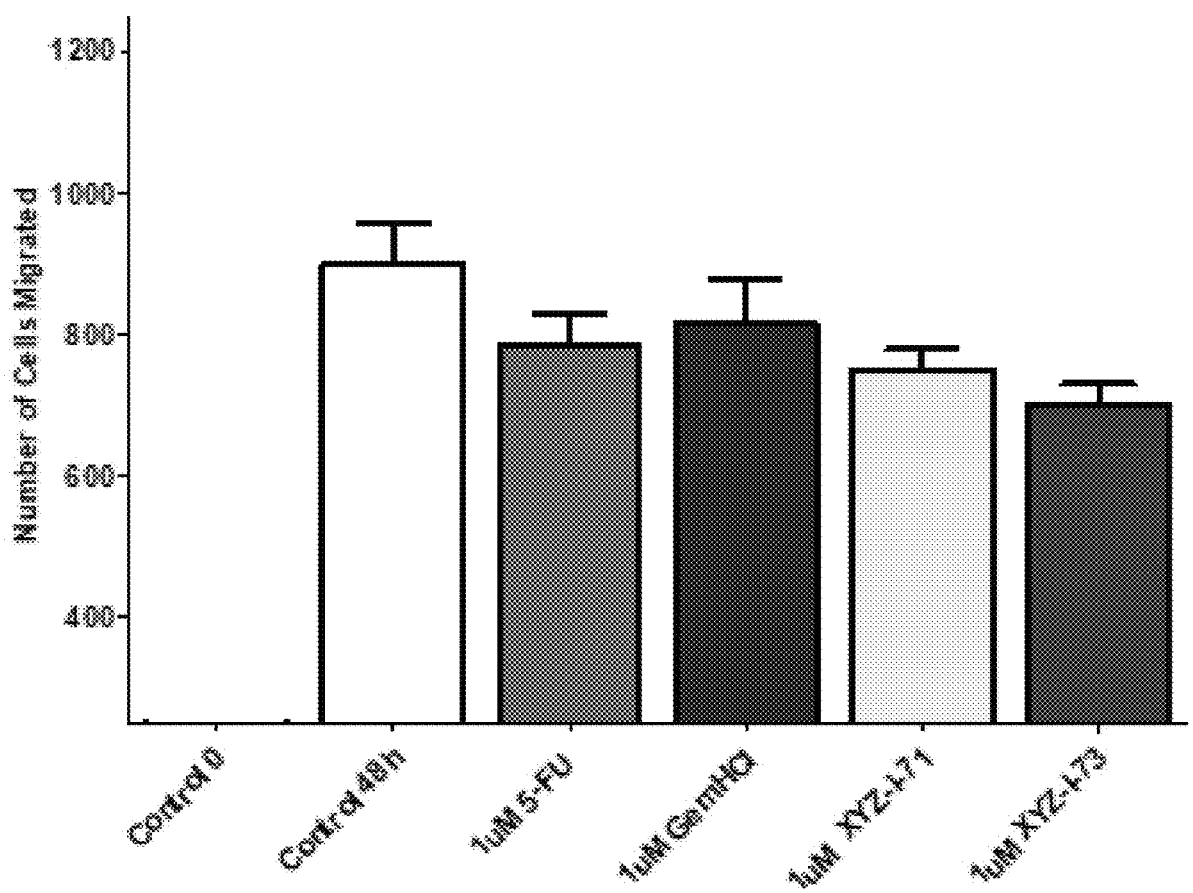
FIG. 9 is a graph depicting number of cells migrated for 5-FU, GemHCl, XYZ-I-71 and XYZ-I-73 on MiaPaCa-2 cells at 1 µM concentration. The results are expressed as the means (±SEM, N=4) relative to the control.
Figure 10:
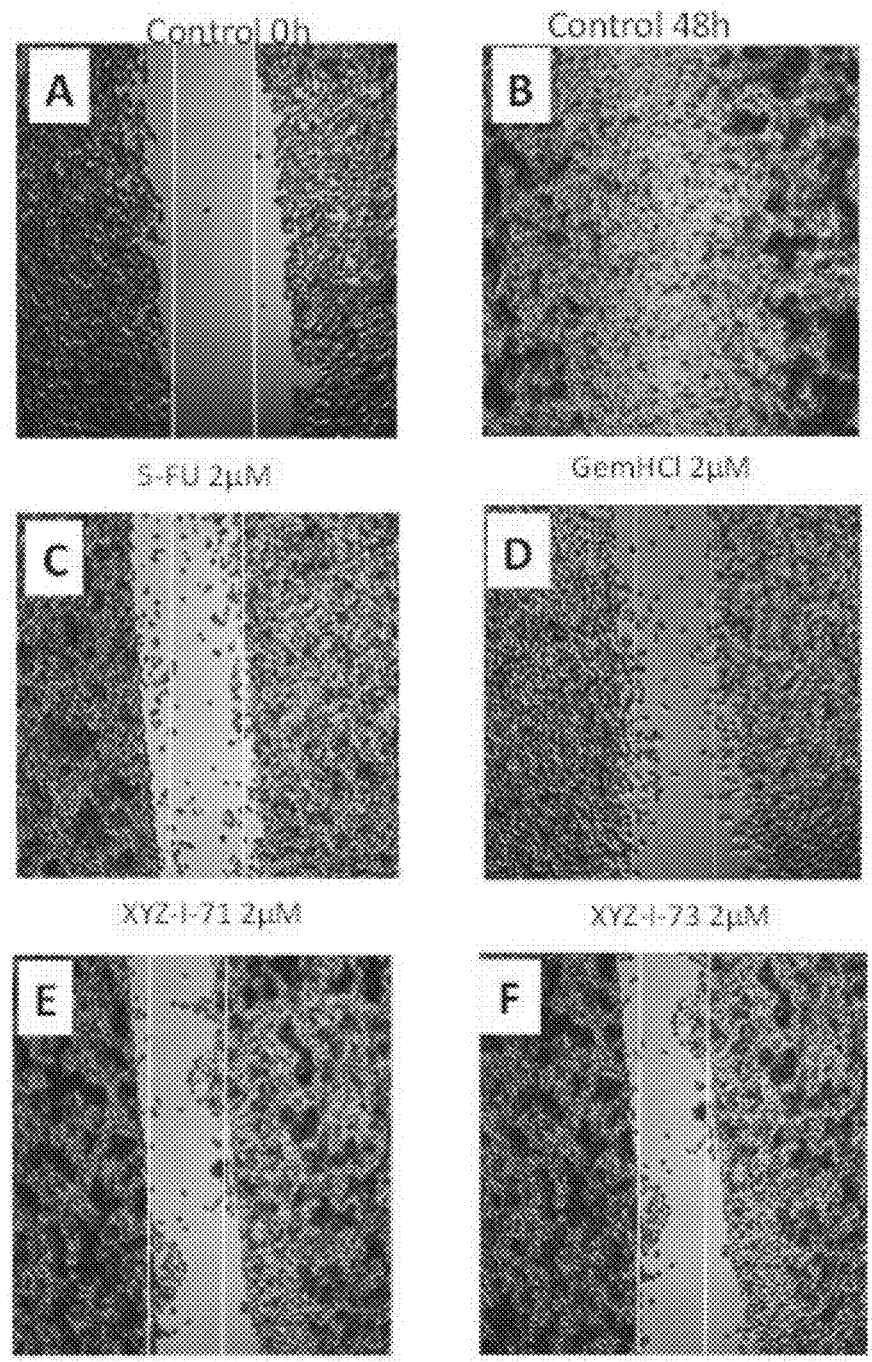
FIG. 10A-F are a series of images depicting migration studies of (A) Control at 0 h; (B) Control at 48 h; (C) 5-FU; (D) GemHCl; (E) XYZ-I-71; and (F) XYZ-I-73 on MiaPaCa-2 cells at 2 µM concentration.
Figure 11:
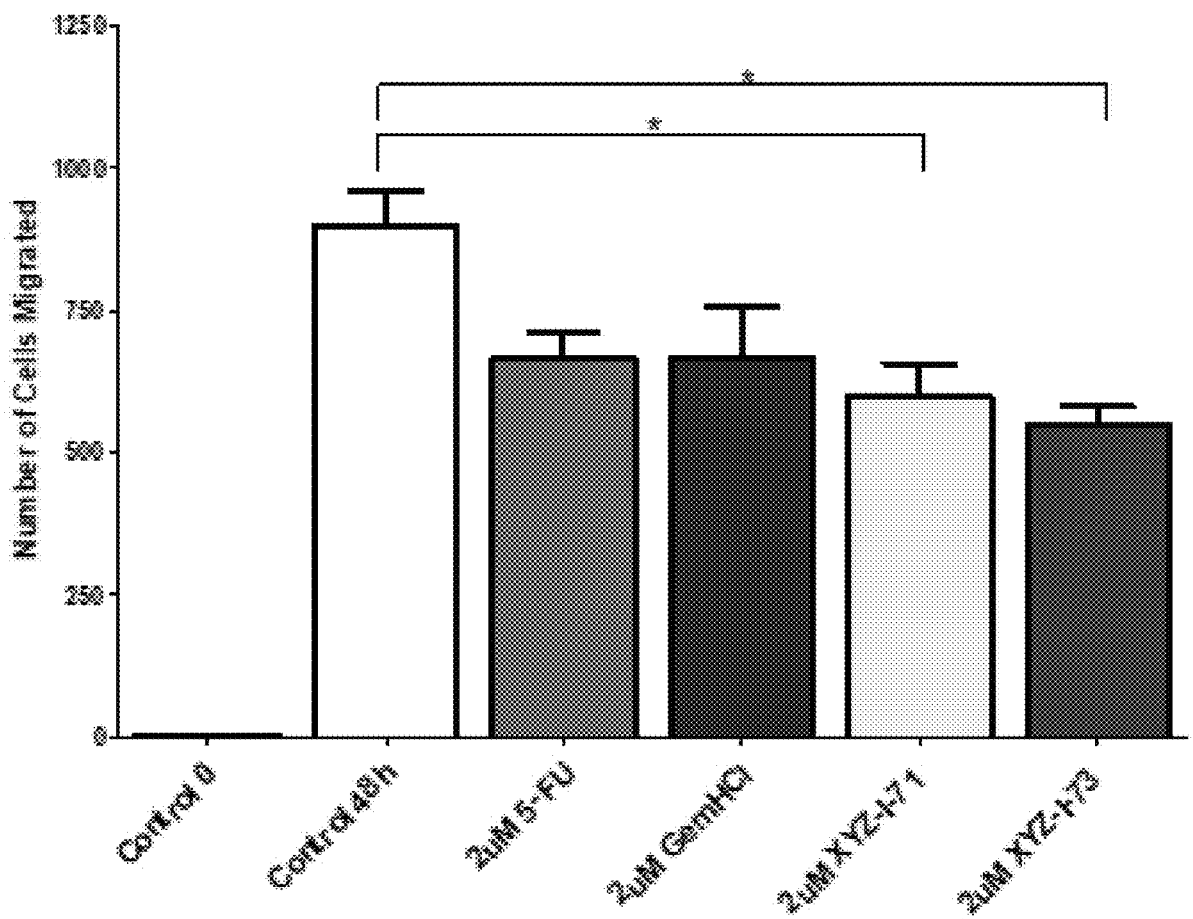
FIG. 11 is a graph depicting number of cells migrated for 5-FU, GemHCl, XYZ-I-71 and XYZ-I-73 on MiaPaCa-2 cells at 2 µM concentration. The results are expressed as the means (±SEM, N=4) relative to the control. Significance (*p<0.01) was determined by One way ANOVA.
Figure 12:
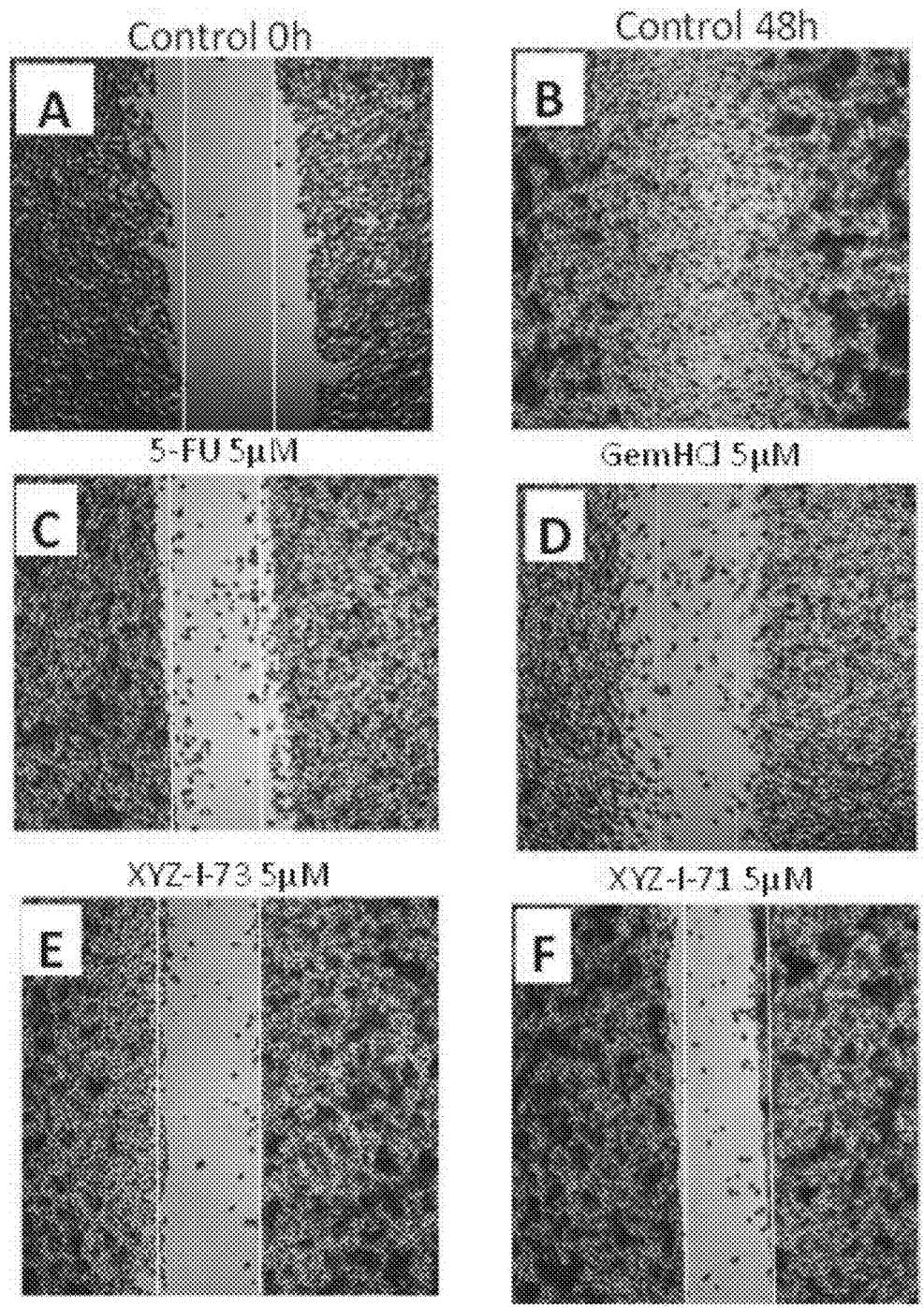
FIG. 12A-F are a series of images depicting migration studies of (A) Control at 0 h; (B) Control at 48 h; (C) 5-FU; (D) GemHCl; (E) XYZ-I-71; and (F) XYZ-I-73 on MiaPaCa-2 cells at 5 µM concentration.
Figure 13:
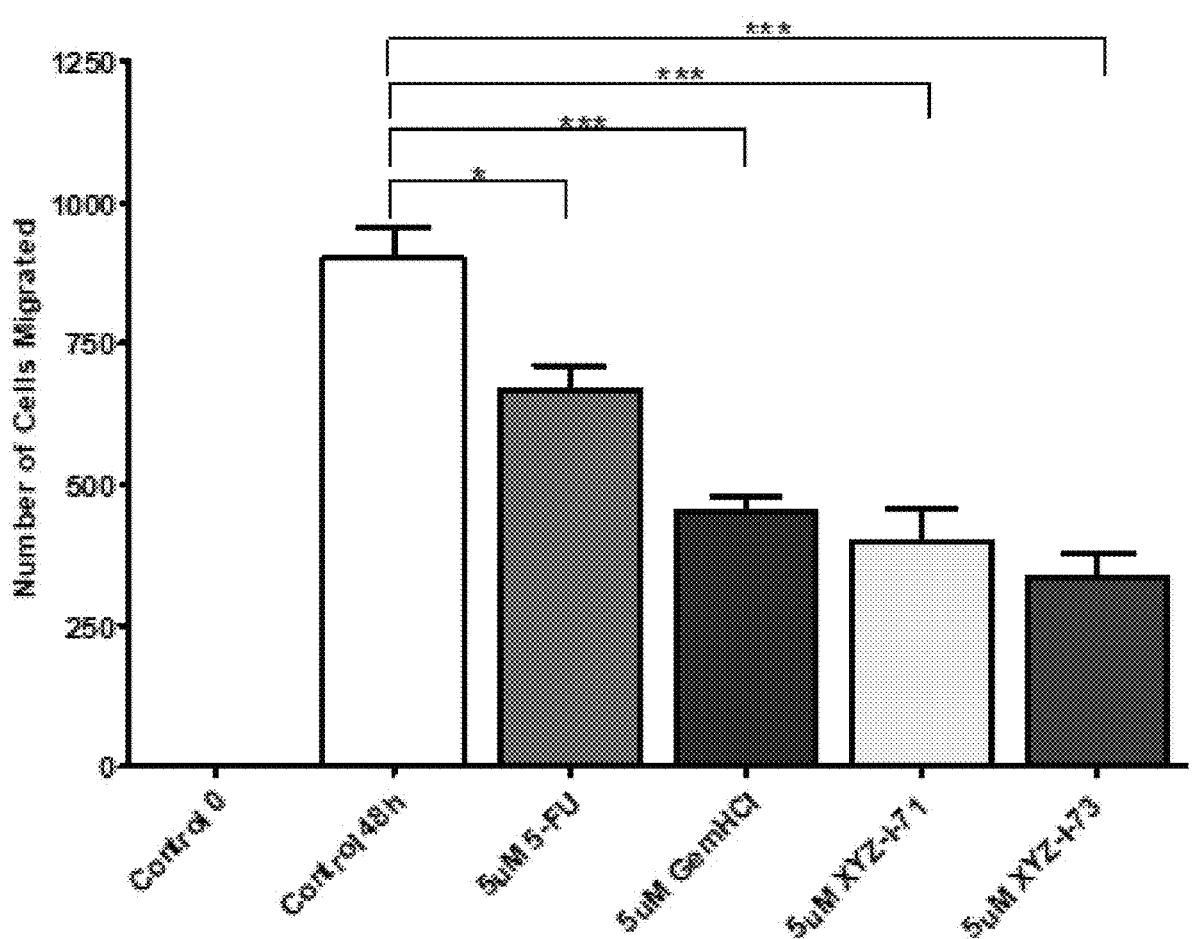
FIG. 13 is a graph depicting number of cells migrated for 5-FU, GemHCl, XYZ-I-71 and XYZ-I-73 on MiaPaCa-2 cells at 5 µM concentration. The results are expressed as the means (±SEM, N=4) relative to the control. Significance (*p<0.0001) was determined by One way ANOVA.
Figure 14:
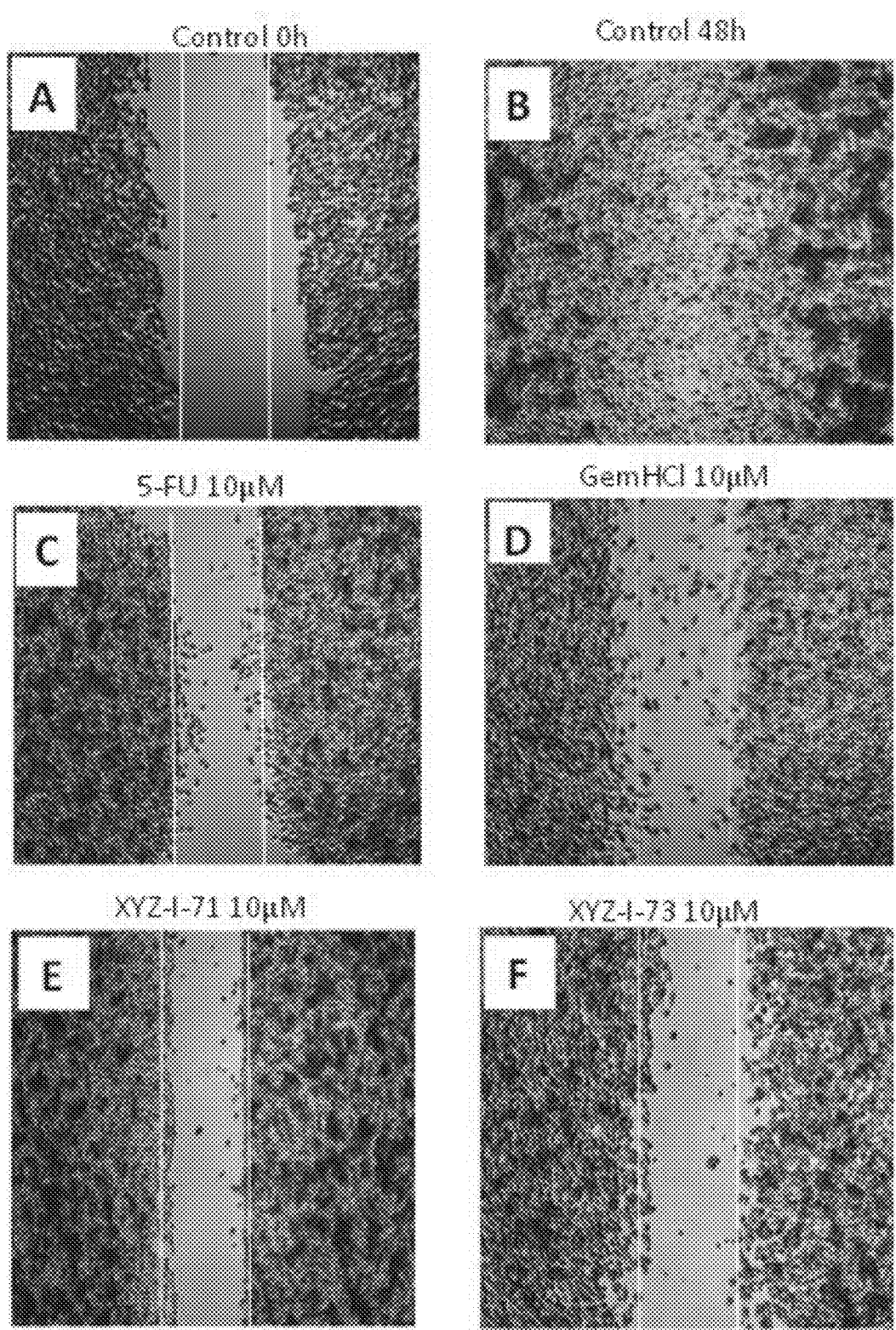
FIG. 14A-F are a series of images depicting migration studies of (A) Control at 0 h; (B) Control at 48 h; (C) 5-FU; (D) GemHCl; (E) XYZ-I-71; and (F) XYZ-I-73 on MiaPaCa-2 cells at 10 µM concentration.
Figure 15:
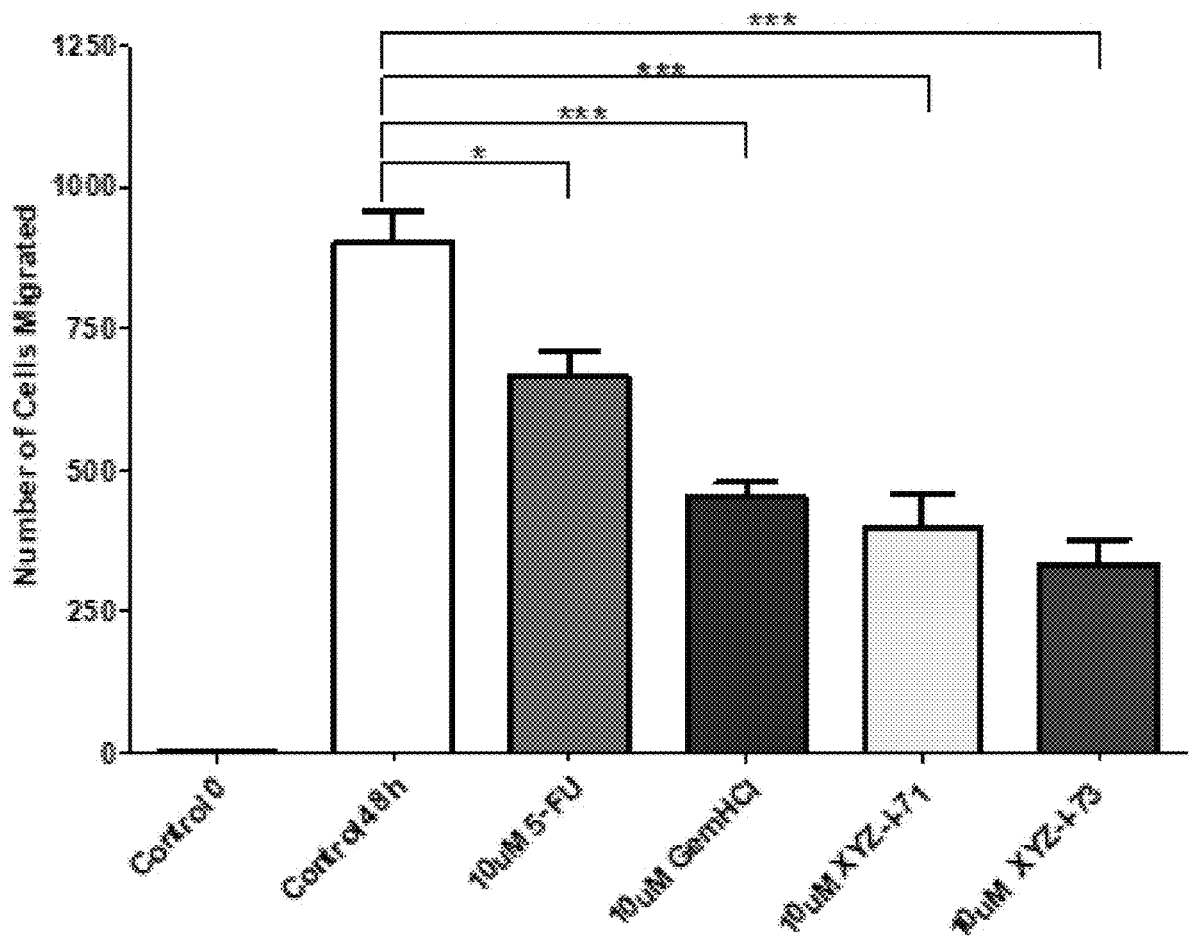
FIG. 15 is a graph depicting number of cells migrated for 5-FU, GemHCl, XYZ-I-71 and XYZ-I-73 on MiaPaCa-2 cells at 10 µM concentration. The results are expressed as the means (±SEM, N=4) relative to the control. Significance (*p<0.0001) was determined by One way ANOVA.
Figure 16:
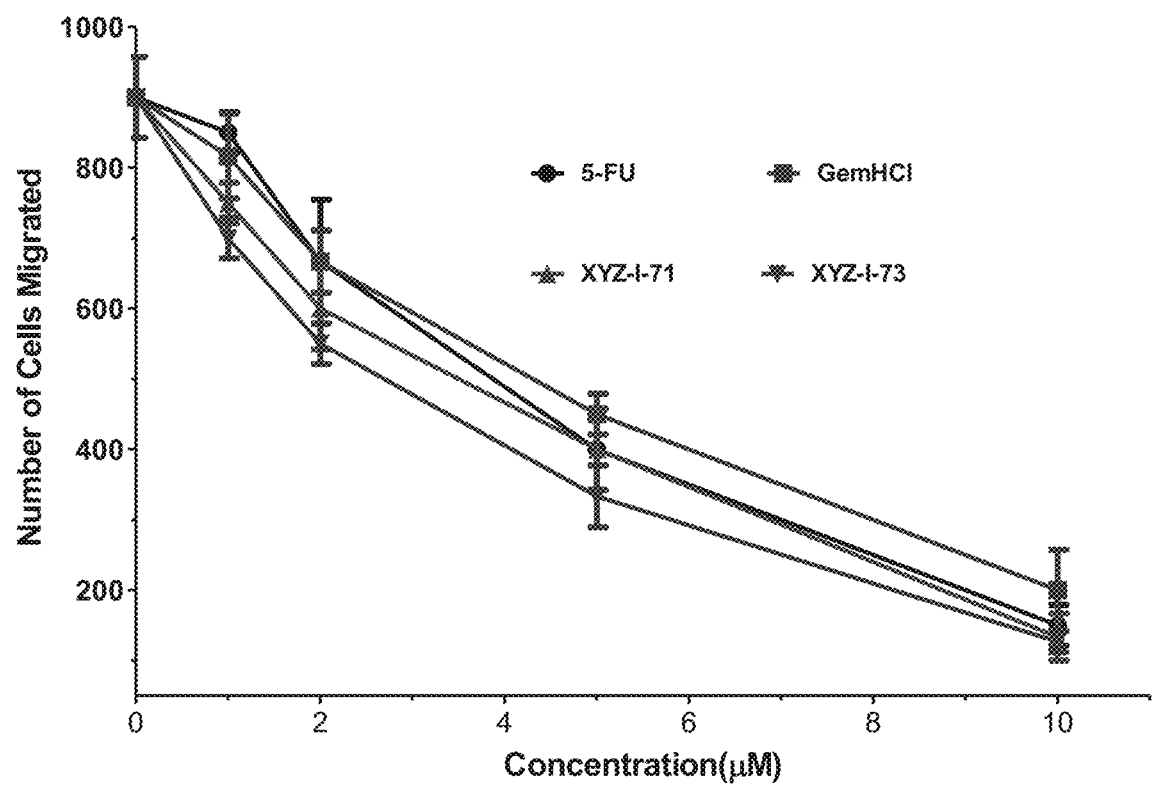
FIG. 16 is a graph depicting the number of cells migrated for 5-FU, GemHCl, XYZ-I-71 and XYZ-I-73 on MiaPaCa-2 cells at varying concentrations (1, 2, 5 and 10 µM) concentrations.

Both of the two new, synthesized fluoropyrimidine nucleosides XYZ-I-71 and XYZ-I-73 have shown promising cytotoxic activity against MiaPaCa-2 cancer line with IC$_{50}$ values of 13.75±1.1 μm and 6.81±1.1 μm respectively, while XYZ-I-73 has shown significant higher cytotoxic activity (see FIG. 7). After comparing the IC$_{50}$ data with 5-FU's, the new synthesized fluoropyrimidine nucleosides XYZ-I-71 and XYZ-I-73 have shown greater efficacy against MiaPaCa-2 cancer line. IC$_{50}$ values are listed in Table 3.

TABLE 3

IC$_{50}$ values (μM) against MiaPaCa-2 cell line as determined by cell viability studies

| Compound | XYZ-I-71 | XYZ-I-73 | 5-FU | Irinotecan | GemHCl |
|---|---|---|---|---|---|
| IC$_{50}$ (μM) | 13.75 ± 1.7 | 6.81 ± 2.1 | 51.07 ± 1.1 | 28 ± 1.5 | 25.29 ± 1.3 |

Example 4—In Vitro Cell Migration Studies—Testing the Efficacy of Compounds XYZ-I-71 and XYZ-I-73 Against MiaPaCa-2 Pancreatic Cancer Cell Line Results Cell migration assay reveals cells ability to move individually or in clusters towards wound made in confluent plate of cells. A uniform scratch was made in 90% confluent monolayer culture of MiaPaCa-2 cells and the extent of closure was monitored under microscope and photographed. Figures (8-13) shows 5-FU, GemHCl, XYZ-I-71 and XYZ-I-73 treatments were used at varying concentration (1, 2, 5 and 10 μM). Migrated cells within the scratch were quantified and the distance of migration measured using NIH ImageJ software. XYZ-I-71 and XYZ-I-73 MiaPaca-2 treatments at (2, 5 and 10 μM) significantly inhibited the number of migrated cells towards the wound compared with the 5-FU, GemHCl after 48 h. Over the same incubation time, the cells in the control group (48 h) migrated farther achieving a complete or near closure of the wounds. The results are expressed as the means (±SEM, N=4) relative to the control.

Methods

Cell migration assay was conducted to determine the effect of on 5-FU, GemHCl, XYZ-I-71 and XYZ-I-73 MiaPaCa-2 cell motility. Ibidi cell culture inserts were used to generate two confluent monolayers of cells separated by a "wound" for this assay. The cells were seeded in 24-well plates at a cell density of 2.5×10$^5$, for 24 h at 37° C. At 75% confluency, cells formed adherent monolayers on either side of the tissue culture insert. Prior to treatment, the cells were serum-starved by replacing complete media with base media (DMEM) and then further incubated for 24 hours. After serum starving, the insert was gently removed to generate a gap or "wound' between the two confluent layers of cells. The monolayers were washed with experimental media and afterwards cells were exposed to varying concentrations of 5-FU, GemHCl, XYZ-I-71 and XYZ-I-73 (1, 2, 5 and 10 μM). Images of the cells invading the wound were captured with an Olympus DP70 Camera.

Example 5—Treatment of Pancreatic Cancer with XYZ-71 (Prophetic)

A 60 year old male presents with jaundice and sudden weight loss. A diagnosis of pancreatic cancer is made via biopsy. The patient is administered a composition having a therapeutically effective amount of N-(5-fluoro-2-oxo-1-(tetrahydrofuran-2-yl)-1,2-dihydropyrimidin-4-yl)octanamide (Compound XYZ-71) for a time period sufficient to treat the cancer. The patient's symptoms are alleviated and the patient is diagnosed as being in remission.

Example 6—Treatment of Pancreatic Cancer with XYZ-73 (Prophetic)

A 65 year old male presents with jaundice, nausea, vomiting, and weight loss. A diagnosis of pancreatic cancer is made via biopsy. The patient is administered a composition having a therapeutically effective amount of N-(5-fluoro-2-oxo-1-(tetrahydrofuran-2-yl)-1,2-dihydropyrimidin-4-yl)dodecanamide (Compound XYZ-73) for a time period sufficient to treat the cancer. The patient's symptoms are alleviated and the patient is diagnosed as being in remission.

CONCLUSION

The inventors have synthesized novel fluoropyrimidine nucleosides that exhibit increased cytotoxic activity against a pancreatic cancer cell line as compared to known cancer treatments of 5-FU and gemcitabine. These new drugs are orally available which avoids the damage to intestinal mucosa by first-pass metabolism, reduces toxicity to a maximum extent, and reduces side effects in the GI tract. The new drugs have a prolonged half-life and keep lower peak concentration of 5-FU in blood stream which lowers the toxicity, elevates the therapeutic index, improves patient response rate, and reduces the side effects. While the drugs were tested in a pancreatic cancer cell line, this use is exemplary and other cancers are contemplated for treatment as enumerated herein.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A composition comprising Formula (I):

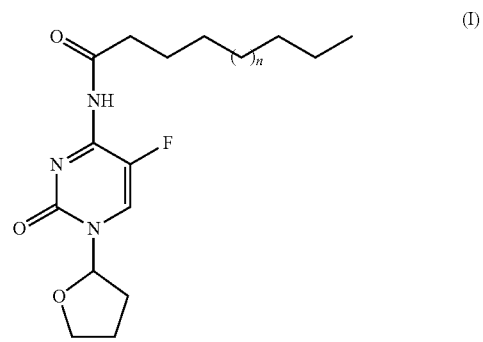

wherein n is an integer from 1 to 5.

2. The composition of claim 1, further comprising a pharmaceutically acceptable carrier.

3. The composition of claim 1, wherein n is 1.

4. The composition of claim 1, wherein n is 5.

5. A method of inducing cytotoxicity in pancreatic cancer cells comprising: administering to the pancreatic cancer cells a therapeutically effective amount of a composition comprising Formula (I):

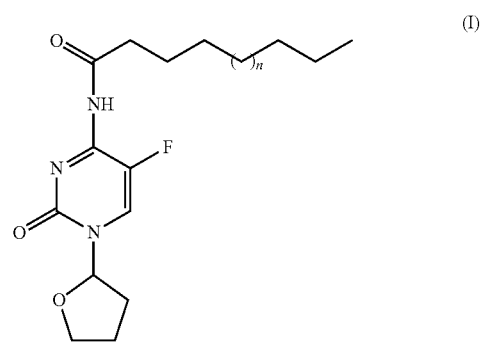

wherein n is an integer from 1 to 5; and
a pharmaceutically acceptable carrier;
wherein administration of the therapeutically effective amount of the composition induces cytotoxicity in the pancreatic cancer cells, thus reducing an amount of the pancreatic cancer cells.

6. The method of claim 5, wherein n is 1.

7. The method of claim 5, wherein n is 5.

8. A method of treating pancreatic cancer in a human patient in need thereof comprising:
   administering to the human patient a therapeutically effective amount of a composition comprising

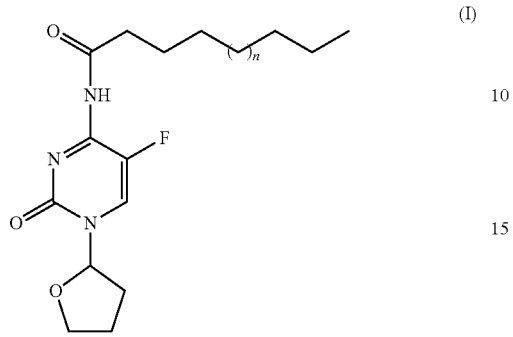

wherein n is an integer from 1 to 5; and
a pharmaceutically acceptable carrier;
wherein administration of the therapeutically effective amount of the composition induces cytotoxicity to treat the pancreatic cancer.

9. The method of claim 8, wherein n is 1.

10. The method of claim 8, wherein n is 5.

* * * * *